United States Patent [19]

Lewis et al.

[11] Patent Number: 5,762,611

[45] Date of Patent: Jun. 9, 1998

[54] EVALUATION OF A SUBJECT'S INTEREST IN EDUCATION, TRAINING AND OTHER MATERIALS USING BRAIN ACTIVITY PATTERNS

[75] Inventors: Gregory W. Lewis, Solana Beach; David L. Ryan-Jones, Ramona, both of Calif.

[73] Assignee: The United States of America as represented by the Secretary of the Navy, Washington, D.C.

[21] Appl. No.: 748,224

[22] Filed: Nov. 12, 1996

[51] Int. Cl.[6] .................................................. A61B 5/0484
[52] U.S. Cl. ............................................ 600/544; 600/545
[58] Field of Search .................................... 600/544, 545, 600/26–28, 558

[56] References Cited

U.S. PATENT DOCUMENTS

| | | |
|---|---|---|
| 4,332,566 | 6/1982 | Mazeski et al. . |
| 4,955,388 | 9/1990 | Silberstein . |
| 5,325,862 | 7/1994 | Lewis et al. . |
| 5,339,826 | 8/1994 | Schmidt et al. . |
| 5,363,858 | 11/1994 | Farwell .................................. 600/544 |
| 5,447,166 | 9/1995 | Gevins . |
| 5,460,184 | 10/1995 | Sato et al. . |

OTHER PUBLICATIONS

Papanicolaou, 1984, "Probe Evoked Potentials: Theory, Method and Applications", *Intern. J. Neurodcience*, pp. 107–131, vol. 24.

Wickens, 1980, "The Structure of Attentional Resources", *Attention and Performance VIII*, pp. 239–257.

Wickens, 1984, "Processing Resources in Attention", *Varieties of Attention*, pp. 63–102.

Jasper, 1958, "The ten-twenty electrode system of the International Federation", *Electroencephalography and Clinical Neurophysiology*, pp. 371–375, vol. 10.

Lewis, 1983, "Event Related Brain Electrical and Magnetic Activity: Toward Predicting On-Job Performance", *Intern. J. Neuroscience*, pp. 159–182, vol. 18.

Lewis et al., 1985, "Few-Trial Evoked Field Stability Using the DC Squid", *Biomagnetism: Application & Theory*, pp. 343–347.

Lewis et al., Aug. 27–30, 1987, "Evoked Neuromagnetic Fields: Implications for Indexing Performance", *Biomagnetism '87*, pp. 266–269.

Lewis et al., 1989, "Evoked Brain Activity and Personal Performance", *Testing: Theoretical and Applied Perspectives*, pp. 97–131.

Lewis et al., 1989, "Temporal Variability of the Neuromagnetic Evoked Field: Implications for Human Performance Assessment", *Advances in Biomagnetism*, pp. 217–220.

*Primary Examiner*—Jennifer Bahr
*Assistant Examiner*—David M. Ruddy
*Attorney, Agent, or Firm*—Harvey Fendelman; Michael A. Kagan; Peter A. Lipovsky

[57] ABSTRACT

The objective evaluation of a subject's interest in specific information, such as education and training materials, for example, is made possible by using patterns of physiological activity generated in the brain. Samples of individual brain activity are obtained to assess whether an individual is paying attention and showing interest in certain materials. Effectiveness in presenting such materials would be improved when direct brain recording activity shows increased interest in the presented material.

24 Claims, 9 Drawing Sheets

All Subjects

EVALUATION OF A SUBJECT'S INTEREST IN EDUCATION, TRAINING AND OTHER MATERIALS USING BRAIN ACTIVITY PATTERNS

STATEMENT OF GOVERNMENT INTEREST

The invention described herein may be manufactured and used by or for the Government of the United States of America for governmental purposes without the payment of any royalties thereon or therefor.

INCORPORATION BY REFERENCE

U.S. Pat. No. 5,325,862 issued on Jul. 5, 1994 to inventors Gregory W. Lewis and David Ryan-Jones titled "METHOD AND/OR SYSTEM FOR PERSONAL IDENTIFICATION AND IMPAIRMENT ASSESSMENT FROM BRAIN ACTIVITY PATTERNS" is hereby incorporated by reference into this specification.

BACKGROUND OF THE INVENTION

Traditionally, the evaluation of the effectiveness of education and training materials has depended upon voluntary verbal and written feedback from individuals, usually in the form of questionnaires or tests.

There is a need for improvements to these techniques for assessing the effectiveness of education, training as well as other materials.

SUMMARY OF THE INVENTION

This invention permits the objective evaluation of a subject's interest in specific information, such as education and training materials, for example, using patterns of physiological activity generated in the brain. The brain patterns may be obtained by directly or indirectly recording the electrical or magnetic activity associated with sensory, cognitive, and motor processing in the brain. Such activity may be recorded using sensors placed in, on, or near the scalp or brain.

According to this invention, samples of individual brain activity are obtained to assess whether an individual is paying attention and showing interest in certain materials, such as education and training materials. Effectiveness in presenting such materials would be improved when direct brain recording activity shows increased interest in the presented material.

According to this invention, frequent and rare irrelevant stimuli are presented aperiodically to a subject during what is called a "baseline period". Presentation of this stimuli during this period establishes baseline brain wave signals. In a preferred embodiment of the invention, the irrelevant stimuli take the form of auditory tones of frequent and rare occurrence. Stimuli of a non-auditory nature could also be used, such as, for example, flashes of light. The term brain signals, in the context of this invention, infer or imply evoked or event-related potentials and/or evoked or event-related magnetic fields.

A sensing element made up of one or more electrodes or magnetic sensors are placed appropriately over or on the scalp or skin of a subject to obtain brain signals occurring proximate in time with the rare irrelevant stimuli. Use of the term "proximate in time" in this context is meant to include sensing brain signals immediately after the onset of the rare stimuli or, alternatively, sensing brain signals both immediately after the onset of the rare stimuli as well as immediately before the onset of the rare stimuli. These baseline brain signals are suitably amplified and filtered and are sent to a data acquisition/transformation stage of the invention.

The data acquisition/transformation stage receives the baseline brain signals and is used to sample, convert to digital format, average and store the signals.

The stimulator is also used to present task stimuli to a subject simultaneously with the aperiodically presented frequent and rare irrelevant stimuli. In a preferred embodiment, the task stimuli take the form of video material though other forms of task stimuli may be used. The subject is asked to merely pay attention to the task stimuli but is not required to perform cognitive processing such as answering questions or making decisions regarding what is being observed.

Task stimuli are presented to the subject for a period of time that is described herein as the "task period". The sensing element of the invention is then used to obtain the brain signals of the subject during the task period that occur proximate in time with the rare irrelevant stimuli. The task-related brain signals are suitably amplified and filtered and are sent to the data acquisition/transformation stage of the invention in which these signals are sampled, converted to digital format, averaged and stored.

The data acquisition/transformation stage is used to compare the stored baseline acquired brain signals with those acquired during the presentation of the task stimuli. An assessment of the subject's interest in the task stimuli is then made based upon the difference in magnitude (average value) between the brain signals obtained during the baseline period and those obtained during the task period. The greater this difference, the greater the interest, it is concluded, that the subject has in the task stimuli material.

An object of this invention is to provide a way to of objectively assess the interest a subject expresses in observed materials.

Another object of this invention is to provide a way of utilizing event related potential (ERP), and/or event related field (ERF), waveforms to assess a subject's interest in observed materials.

Yet another object of this invention is to provide a way of utilizing event related potential (ERP), and/or event: related field (ERF), waveforms to assess a subject's interest in observed materials without requiring the subject to perform any cognitive processing while observing the materials.

Other objects, advantages and new features of this invention will become apparent from the following detailed description of the invention when considered in conjunction with the accompanying drawings and appended claims.

DESCRIPTION OF THE PREFERRED EMBODIMENT

For more than 50 years, research has suggested that there are large individual differences in the electrical, and magnetic, activity in the brain. There is also evidence that some of the characteristics of brain activity may be relatively stable when measured from day-to-day. Brain responses to sensory stimulation (e.g. visual, auditory, somatosensory, olfactory, gustatory) as well as higher-order cognitive processing (e.g., decision-making), can now be examined in great detail using a variety of recording procedures.

An on-going record of brain electrical activity records is called an electroencephalogram (EEG), and a comparable record of brain magnetic activity is called a magnetoencephalogram (MEG). Electroencephalogram and MEG records usually have a great deal of uncontrolled variation, and special techniques are necessary to stabilize activity patterns. Such stabilization of brain activity can be provided by strict control of the conditions under which brain responses are generated.

When human sensory systems are stimulated by an event such as a flash of light or a tone, there is a predictable sequence of processing that occurs in the brain. This processing generates an electrical activity within the brain known as an event-related potential (ERP). The ERP can be recorded from the scalp and begins shortly after the onset of stimulation and lasts 1–3 seconds after the stimulation. These ERPs can be repeatedly generated from individuals given the same stimulus. Due to the low amplitude of the ERP brain signal, it is often necessary to repeatedly sample the response to the stimulus, and to average the response patterns. Event-related potential measures are in the microvolt range (uV, millionths of a volt).

Comparable records of averaged magnetic brain activity are called evoked fields or event-related fields (ERFs). Special low-temperature systems have only relatively recently made it possible to measure the low amplitude neuromagnetic signals emitted by brain tissue. The unit of measurement of these signals is the femtoTesla ($10^{-15}$ Tesla).

Neuroelectric and neuromagnetic recordings are subsets of more general measures, called bioelectric and biomagnetic measures. Bioelectric and biomagnetic measures refer to recordings from all types of tissue including neural, muscle, heart, and lungs.

Individual performance levels, including those pertaining to training, are determined by alertness, attention, and the quality and quantity of sensory and cognitive processing. These determining factors may be objectively indexed through neuroelectric and neuromagnetic physiological techniques;.

Neuroelectric recordings (electroencephalogram, EEG) are obtained through contact electrodes attached to the scalp or brain, and reflect minute voltages resulting from brain processing. Neuromagnetic recordings (magnetoencephalography) use cryogenic and superconductivity technology, do not require scalp contact, and measure very minute brain magnetic fields.

General alertness may be measured by on-going EEG activity. In order to effectively measure sensory, and cognitive processing, however, event-related brain potentials (ERP) generally must be obtained. The ERP records can be obtained by presenting stimuli (i.e., visual and/or auditory), and by determining the average of the signals generated from the stimuli. The resulting ERP reflects microvolts voltage deflections from a baseline condition. These deflections appear at fairly specific time points, and are referred to as ERP components.

Figure 1:
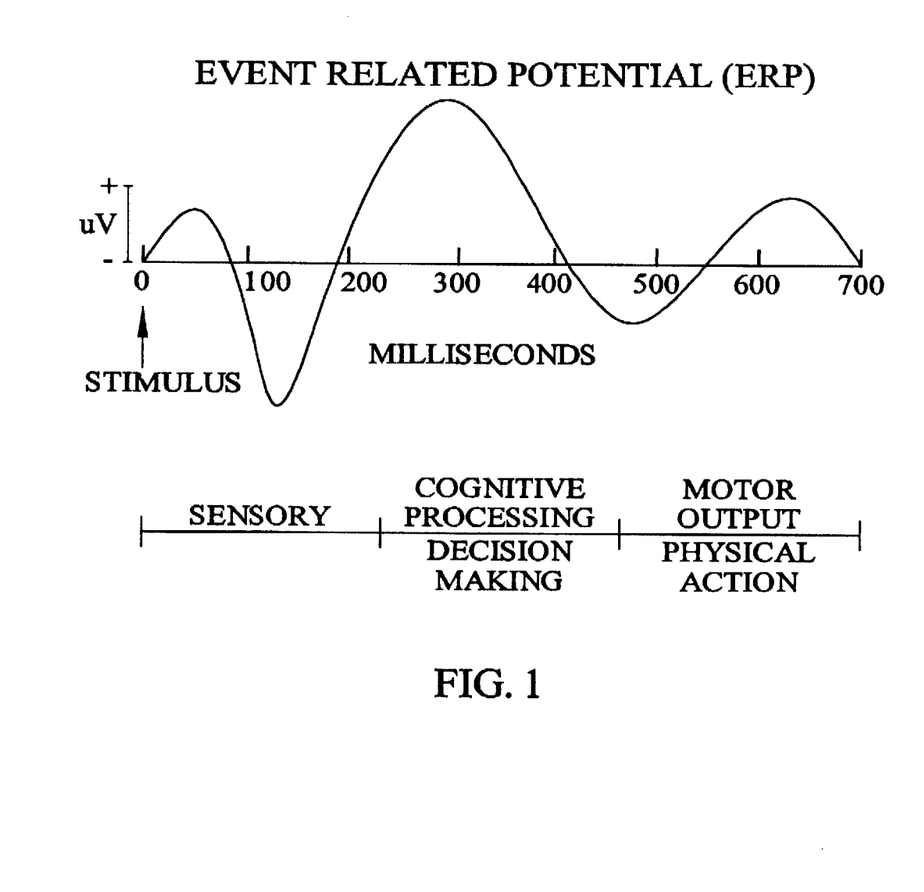
FIG. 1 is an example event-related potential (ERP) illustrating ERP components associated with sensory processing, cognitive (decision making) processing and motor output.

Attention, sensory processing, cognitive (decision making) processing, and motor output are associated with these components, and may be seen in FIG. 1. What is known as probe stimuli are used to generate the ERP and these may be either relevant or irrelevant in nature to the subject. Relevant probe stimuli are those stimuli a subject is required or instructed to pay attention to. Irrelevant probe stimuli are stimuli a subject is asked or otherwise instructed to ignore.

In accordance with an exemplary embodiment of this invention, auditory irrelevant probe stimuli are used to generate ERP records both during baseline and task recording periods. Irrelevant stimuli have the advantage of not otherwise complicating or contaminating a subject's thought processes during the course of testing. An example of an irrelevant probe ERP technique that may be used in this invention is described by Papanicolaou & Johnstone, see Papanicolaou, A. C. & Johnstone, J. (1984) "Probe evoked potentials: Theory, methods, and applications", International Journal of Neuroscience, 24, 107–131.

Even though an individual is instructed to ignore a stimulus, i.e. an irrelevant probe, while the subject is performing a task such as viewing video material, an ERP will still be generated from the irrelevant probe. When a subject does not attend to, or perform a task, called the subject's baseline condition, most resources will be available to process the irrelevant probe, and will result in larger irrelevant probe ERP components. As interest is increased in the task, attentional and/or cognitive resources will be diverted from the irrelevant probe to the task, and will produce a corresponding decrease in ERP component amplitudes. These changes are related to the resources devoted to the task, and are considered to be a measure of interest in the task.

It is known that the amplitude of the ERP components is usually large when mental resources are dedicated solely to the irrelevant tones. When the subject diverts his resources from the tones to a primary task, such as viewing video material, the ERP component amplitudes decrease. This amplitude decrease reflects the allocation of mental resources from the tones to the task, such as the observing of video material. If the shift in mental resources from the baseline to the video material is minimal (subject does not have interest), the ERP amplitude will not decrease. Greater decrease goes with greater shift in mental resources or interest.

The theoretical foundation for the invention lies in the resource allocation model of cognitive processing proposed by C.D. Wickens, see Wickens, C. D. (1980), "The structure of attentional resources", In R. Nickerson & R. Pew (Eds.). Attention and performance VIII. New Jersey: L. Erlbaum & Associates and Wickens, C. D. (1984), "Processing resources in attention", In R. Parasuraman & D. Davies (Eds.). Varieties of Attention. Orlando: Academic Press.

In accordance with the invention, when a subject performs a primary task, such as viewing video material, he may also be presented with auditory tones, considered to be irrelevant stimuli. Allocation of mental resources may be measured by obtaining ERP data generated by the irrelevant stimuli probes.

In an exemplary embodiment of the invention demonstrated for feasibility purposes, most (greater than fifty percent) of the tone probes used were at 1500 Hz frequency. These were designated the "frequent" stimuli. However forty percent of the tone probes were at another frequency, one octave lower (750 Hz), designated as the "rare" stimuli. The particular frequencies of the tones are not considered to be crucial, only that the tones are different, such as being one octave apart. The tones were 50 ms in duration with 10 ms rise and decay duration. Both tones had the same intensity of about 75 dB(A). Background ambient sound level was about 65 dB(A). The subjects were instructed to ignore and not respond to the irrelevant tone probes throughout a data recording session.

Task stimuli took the form of video tape material that was presented to the subjects under test. The video material included two 30-second video segments. One video segment was selected from material produced by the commercial television and advertising industry under the label of Partners for a Drug Free America. A second video segment was treated as a video material "control," and dealt with Olympic athlete performance. During the video "task" segments, the subjects were to ignore and not respond to the irrelevant tone probes presented during the video segments, and, in a departure from the prior art, were not required to perform any cognitive processing during the video segments, such as answering questions either mentally, verbally or non-verbally.

Twenty six subjects were tested. The age of this group of subjects was 26.6+/-7.4 years.

After the video segments were shown to each subject and ERP recording had ended, a confirmation step was conducted in which questionnaires were given to the subjects to categorize the subject according to their perceived interest in the video material.

Questionnaire scores were determined from a scale of 1 to 7 for questions related to interest, effectiveness, accuracy information content, and realism of the video material. These four questions were determined to contribute significantly to the statistical variance using factor analysis and were used to develop two interest groupings of subjects denoted as HIGH and LOW. Half of the 26 subjects were assigned to the HIGH group and half to the LOW group based on the questionnaire factor analysis scores.

For the question regarding "interest," the scale ranged from 1 (very boring) through 4 (neutral) to 7 (very interesting). "Effectiveness" was determined from the scale of 1 (very ineffective) through 4 (neutral) to 7 (very effective). "Information" was graded on the scale of 1 (very inaccurate) through 4 (neutral) to 7 (very accurate). "Realism" was graded on the scale of 1 (very unrealistic) through 4 (neutral) to 7 (very realistic).

Other information was ascertained by way of the questionnaire, such as whether the main characters of the videos were likable, quality of the video subject matter, and whether the mood of the material was serious or light hearted, but this information was not used in differentiating subjects within the group because the information was not found to contribute significantly to the statistical variance.

Recordings during both baseline and task periods were obtained from three sites on the scalp (to be described further) lying over the frontal (FZ), central (CZ), and parietal (PZ) regions of the brain, see Jasper, H. (1958), "The ten-twenty electrode system of the International Federation". Electroencephalography and Clinical Neurophysiology, 10, 371-375.

These sites were specifically selected to maximize sensitivity to recording information related to attention, interest, and alertness. The inventors consider that additional recording sites may improve data analysis precision. All cortical electrodes were digitally re-referenced to linked mastoid regions (behind the ears). Sampling rate was 128 Hz.

Figure 2:
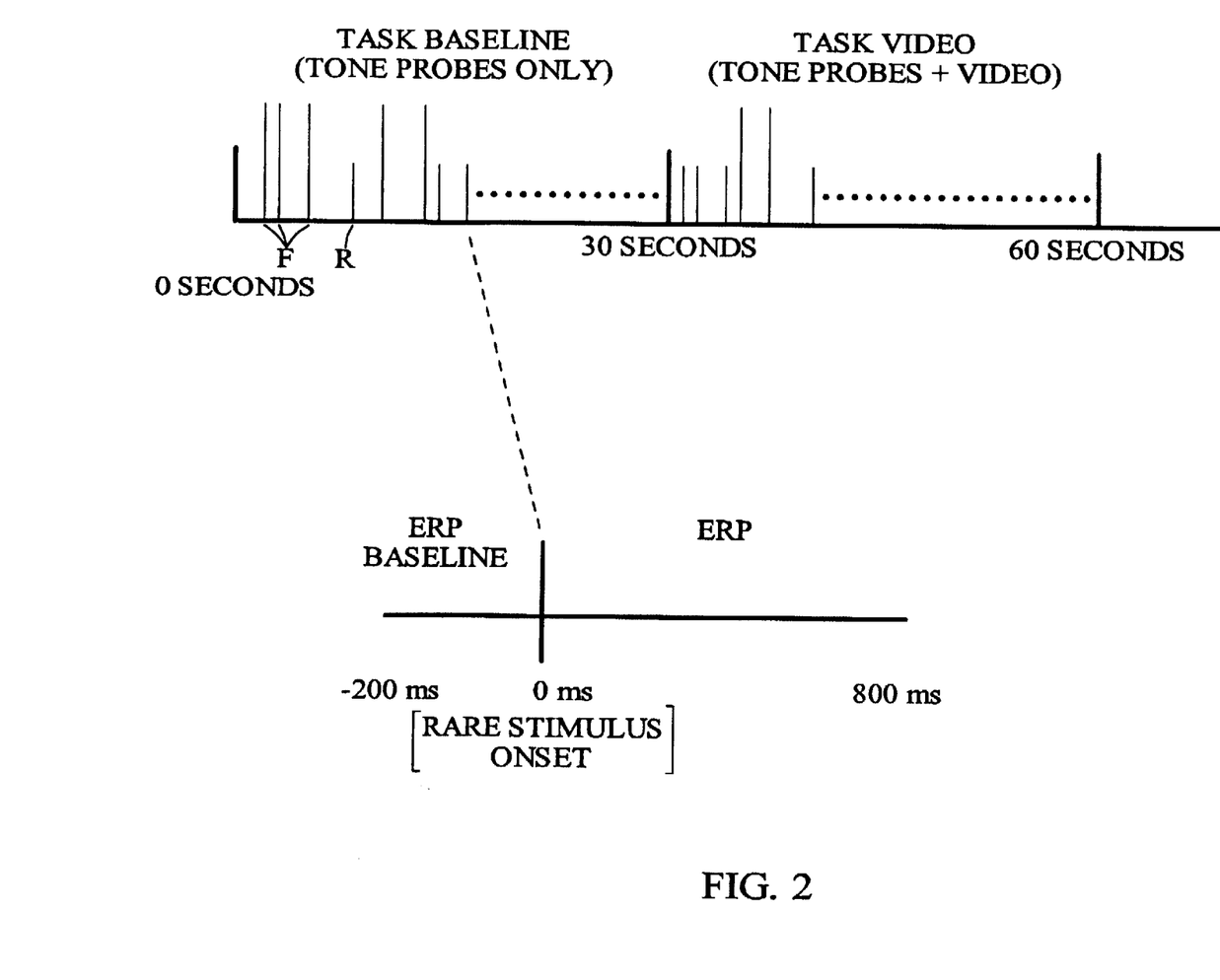
FIG. 2 are time lines as may be used in the invention in which the occurrences of exemplary stimulus events and recording times relating thereto are illustrated.

Referring to FIG. 2, prestimulus ERP activity (that which occurred prior to the rare stimulus onset) was recorded for 200 ms, while poststimulus activity (that which occurred after the rare stimulus onset) was recorded for 800 ms (shown at the bottom of this figure). The auditory probe rare (R) and frequent (F) stimuli were presented aperiodically at an inter-trial interval (ITI) of 1000 ms with a variance of +/-100 ms with as little as 1 ms differential. Recording time included a minimum of 30 seconds of auditory probe baseline, followed by 30 seconds of recording during the presentation of the video material.

All electrophysiological data were recorded as continuous on-going EEG activity with stimulus trigger marks noted In addition to the three recording sites, two mastoid reference sites (to be described further) were used for digitally re-referencing the EEG channels. Such re-referencing is explained further in U.S. Pat. No. 5,325,862 incorporated by reference herein. Horizontal electrooculogram (HEOG) and vertical electrooculogram (VEOG) data also were recorded.

Several steps were taken in preprocessing the electrophysiological data. The first step was to copy the original continuous data file for back-up purposes. The scalp electrode sites had eyeblink and eye movement artifacts corrected by way of software to be described. Bandpass filtering was done on the on-going activity with roll-off characteristics of 24 dB/octave. As previously described, these data were epoched from 200 ms prestimulus (-200 ms) to 800 ms poststimulus. Baseline correction (normalization) was performed based on prestimulus activity from -100 ms to stimulus onset.

The electrophysiological data were stored at each of these stages for data security reasons, and also to permit the returning to and the reanalyzing of the data at specific stages if required.

Sorting of the epochs by stimulus condition and stimulus type was then performed. Sorting by condition provided the baseline versus video (task) recording period comparisons, while sorting by stimulus type allowed examination of the "rare" versus "frequent" stimulus conditions. The desired signal-to-noise ratio, variance, signal averaging (magnitude determination), and other analytic procedures were then performed on the data by way of software to be described. In a preferred embodiment of the invention, only the brain signals obtained during the "rare" stimuli epochs were used to construct the ERP averages that served as a basis to assess a subject's interest.

Figure 3:
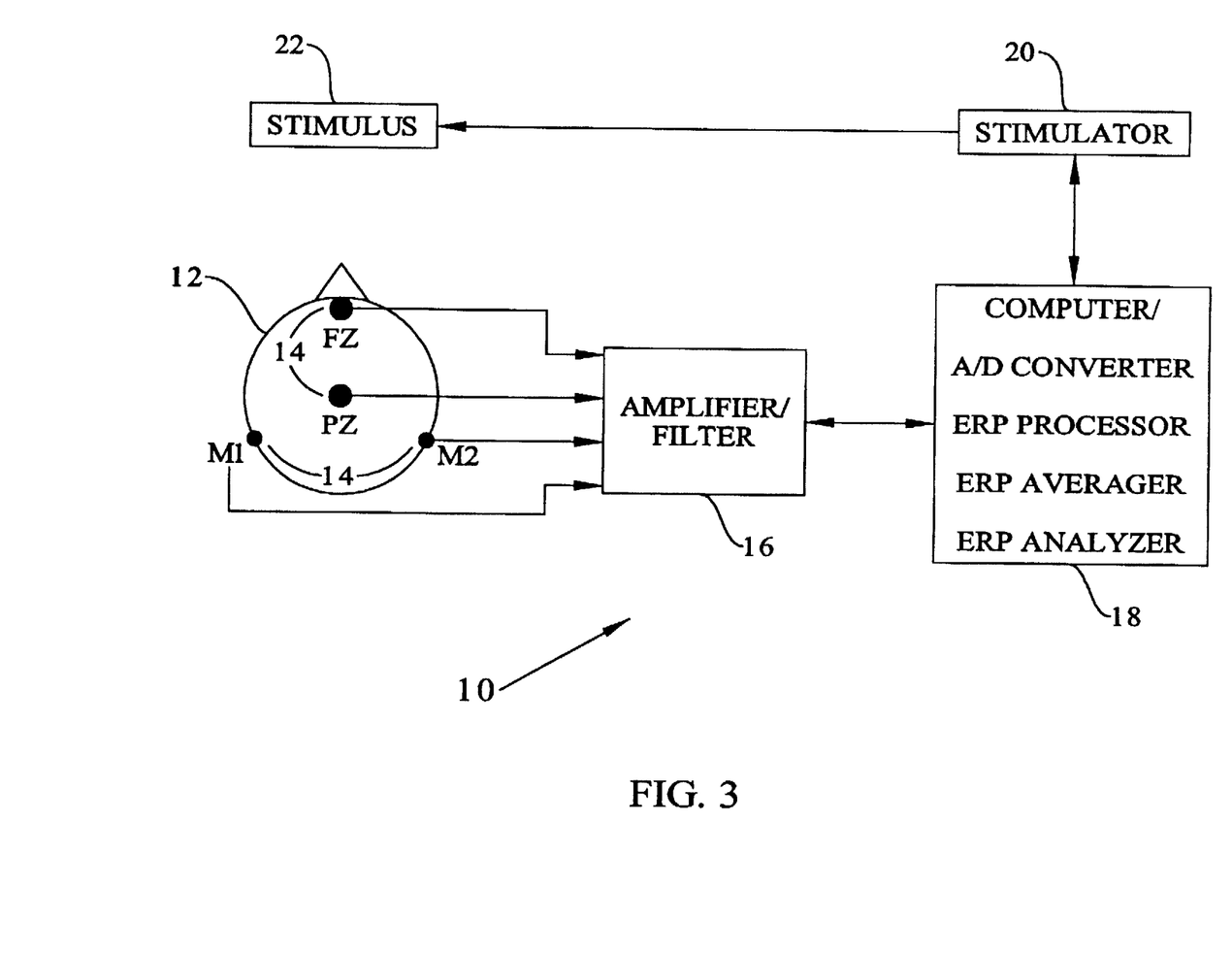
FIG. 3 is a schematic representation of an exemplary apparatus as may be used in accordance with the invention.

In FIG. 3, an exemplary schematic of one embodiment 10 of the invention is shown as may be utilized to assess a subject's interest in training, educational and/or other materials. An individual subject 12 is "wired" or otherwise hooked to a brain signal sensing element of the invention such as one including electrodes 14 placed on the scalp to obtain electrical brain signals. In the case in which magnetic brain activity is desired to be sensed, the sensing element of the invention will include magnetic sensors mounted above scalp recording sites. Exemplary electrodes suitable for electrical brain signal recording purposes are commercially available as units such as those marketed by Electro-Cap International of Saxton, Ohio and are made of tin to minimize polarization. A wide variety of electrodes or sensors fabricated from a number of appropriate materials may be used to obtain the brain signals utilized in the invention. Electrodes 14 are attached to the scalp of subject 12 using a suitable electrolyte material available through a number of commercial sources such as Electro-Cap International and are positioned to conform to the location standards of the 10/20 International System (Jasper, 1958) referred to above.

Referring again to FIG. 3, in the system of the invention constructed for feasibility purposes, four scalp recording sites were used. Frontal (FZ), Pariental (PZ), M1 and M2. The FZ and PZ electrodes were referenced to the left mastoid region (M1), using separate amplifiers for each data recording channel. An additional amplifier recorded electrical voltage from M1 referenced to the right mastoid area (M2). The electrical activity from M1 and M2 were averaged, in a common technique called digital re-referencing.

The electrical voltage picked up by the electrodes is very small (microvolts, millionths of a volt) and it is known that these signals must be amplified and appropriately filtered such as by an amplifier stage 16. As indicated above, one amplifier per electrode/reference pair is typically used. A typical amplifier suitable for this purpose is a model 12A5 made by the Grass Company of Quincy, Mass. Such amplifiers not only amplify the brain activity signal but also provide for a degree of filtering of unwanted signals. Amplifier gain is typically 20000 times and the filter bandpass setting is typically 0.1–100 Hz.

To ensure adequate electrode to scalp contact, electrode impedance is measured prior to recording, such as by way of a Grass impedance meter, model EZM1D. Typical acceptable meter readings are 5K Ohms or less.

The amplified signals are then fed to a computer data acquisition/transformation stage 18. A typical device that could be used for this purpose is a Dell model 325. This unit is based on an Intel 386 CPU that runs at 25 megaHz, has 8 megabytes of random access memory, a 1 gigabyte hard disk, MS DOS 5.0 operating system and a 14" VGA display monitor (0.28" dot pitch) for the researcher/operator convenience. Within data acquisition/transformation stage 18, input analog data are sampled, converted to digital format, averaged and are analyzed. Sampling rate is typically 128 Hz.

Hardware and software that may be used in conjunction with these functions are available through NeuroScan, Incorporated of Herndon, Va. Specifically, NeuroScan's "SCAN" hardware and software subsystem was selected and used to assist in the performance of an embodiment of the invention.

The NeuroScan software is used for processing event-related brain potentials (ERP) by removing unwanted artifacts such as eye blink or muscle movement, and selecting the specific single epochs to be used in ERP averaging. The mechanics of these processes are well established and documented in the literature.

One of ordinary skill in the art will realize that a variety of other electrodes, amplifiers, filters, impedance meters, and computers, disks, memory, operating systems and monitors as well as dedicated hardware/software packages could be selected other than those identified above to appropriately process signals representative of physiological activity in the brain as is done in accordance with this invention.

Auditory stimulator stage 20 is electronically coupled to computer data acquisition/transformation computer 18 and includes its own computer such as a Dell model 325 personal computer with a similar configuration as that of stage 18 except the computer within stimulator stage 20 uses a 340 Mbyte hard disk. Stimulator stage 20 is connected to data acquisition/transformation computer 18 through NeuroScan, Incorporated interface hardware and software. Stimulator 20 provides the auditory stimuli, presented via stimulus unit 22 such as an audio speaker.

Many options are available to provide a variety of stimulus presentation including auditory, visual, psychomotor, complex cognitive tasks, or other scenarios which may be developed by the user. Of course other appropriate software and stimuli could have been chosen to provide the required stimulus information.

Additional description of equipment which may be used in this invention can be found in U.S. Pat. No. 5,325,862 issued to inventors Lewis and Ryan-Jones incorporated by reference herein.

Similar equipment and procedures are used in the recording, processing, and analyzing of neuromagnetic evoked field (EF) data. Descriptions of hardware and software recording equipment and procedures has been published in the open literature see Lewis, G. W., (1983), "Event related brain electrical and magnetic activity: Toward predicting on-job performance", International Journal of Neuroscience, 18, 159–182; Lewis, G., Blackburn, M., Naitoh, P., & Metcalfe, M. (1985), "Few-trial evoked field stability using the DC SQUID", In Weinberg, H., Stroink, G., & Katila, T. Biomagnetism: Applications and Theory. New York: Pergamon Press; Lewis, G. W., Trejo, L. J., Nunez, P., Weinberg, H., & Naitoh, P. (1987), "Evoked neuromagnetic fields: Implications for indexing performance", In Atsumi, K., Kotani, M., Ueno, S., Katila, T., & Williamson, S. J. Biomagnetism '87. Tokyo: Tokyo Denki University Press; Lewis, G. W. & Sorenson, R. C. (1989), "Evoked brain activity and personnel performance", In Dillon, R. F. & Pellegrino, J. W., Testing, Theoretical and Applied Perspectives. New York: Praeger; and Lewis, G. W., Trejo, L. J., Naitoh, P., Blankenship, M., & Inlow, M. (1989), "Temporal variability of the neuromagnetic evoked field: Implications for human performance assessment", In Williamson, S. J., Hoke, M., Stroink, G., & Kotani, M. Advances in Biomagnetism. New.

These publications reported on data using a single channel neuromagnelometer, however, other multi-channel neuromagnetometer systems, such as the BTI model 605, for the recording of EF data over more channels and larger number of brain regions could be used.

Data reported herein are only ERP, however earlier research has suggested that EF data may provide improved personnel assessment due to being non-contact in nature, monopolar, providing improved localization of brain activity, and improved sensitivity to individual subject differences, see (Lewis, 1983).

Figure 4:
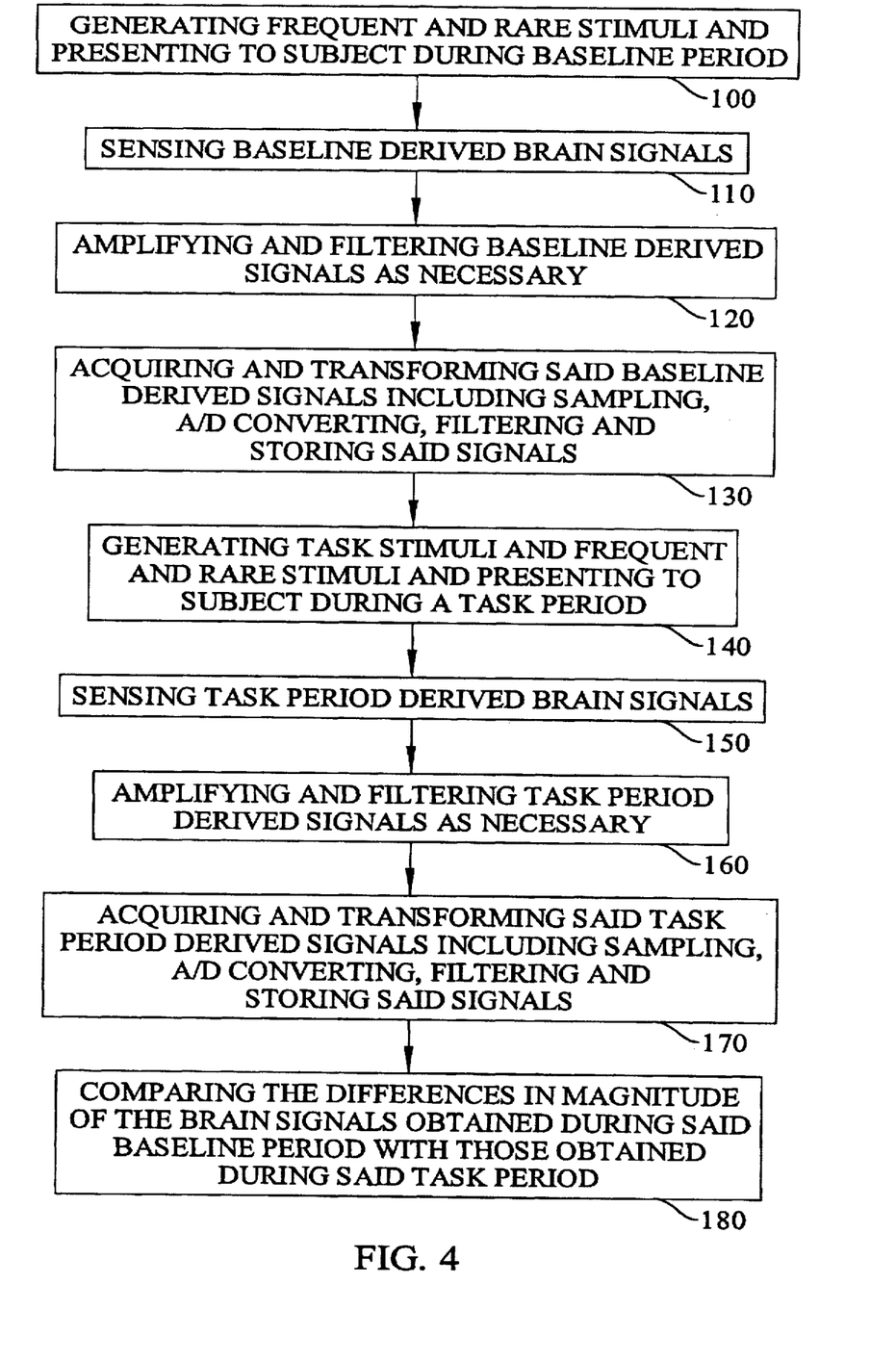
FIG. 4 is a flow chart of an exemplary method by which this invention may be performed.

Referring now to FIG. 4, a process by which the inventive concept of the invention may be carried out is shown. This method provides a way in which a subject's interest in certain materials may be assessed in which the subject is not required to perform any cognitive decision making.

In step 100, a stimulus generator is used to generate frequent and rare stimuli that are presented to a subject during a baseline time period. In a preferred embodiment of the invention, the subject is instructed to ignore the frequent and rare stimuli. The frequent and rare stimuli evoke the generation of signals (brain signals) such as those that take the form of evoked or event-related potentials and/or evoked or event-related magnetic fields.

In step 110, a sensing of the signals takes place such as can be accomplished via a sensing element that includes electrodes and/or magnetic sensors. The baseline-derived signals that are obtained in step 110 are then appropriately amplified and filtered, as necessary, in step 120, for receipt 130 by the data acquisition/transformation stage of the invention. In the data acquisition/transformation stage a transforming of the brain signals obtained during the baseline period takes place. This "transforming" includes sampling the analog signals, converting them to digital format, removing unwanted artifacts and selecting if one desires specific epochs of the signals for further analysis.

In accordance with this invention, epochs of predetermined window length are chosen proximate in time with the rare stimuli presentations. From the brain signals of these epochs, an event-related potential (ERP) average magnitude is determined and is stored for later analysis purposes.

In step 140, the stimulus generator is used to generate task stimuli simultaneously with the aperiodically presented frequent and rare stimuli, these presentations being made to the subject during a task period. Brain signals are thereby evoked within the brain of the subject as a result of the frequent, rare and task stimuli. In this step, according to a preferred embodiment of the invention, no action on the part of the subject is required other than simply observing the task stimuli.

In a preferred embodiment of the invention, the subject is instructed to ignore the frequent and rare stimuli. In addition, the subject is not asked or required to perform any cognitive (decision making) tasks during this step such as taking a test in which the subject could answer questions purely mentally, in writing, verbally or nonverbally.

In step 150, a sensing of the signals occurring during the task period takes place, and, as in step 110 above, is accomplished via the sensing element of the invention that includes electrodes and/or magnetic sensors depending upon the nature of the signals desired to be detected. The task-period derived brain signals that are obtained in step 150 are then appropriately amplified and filtered, if necessary, in step 160, for receipt 170 by the data acquisition/transformation stage of the invention. As in the data acquisition/transformation step 130 above, similar transforming of the brain signals takes place, however in this stage the brain signals obtained during the task period are transformed. As in step 170, brain signals generated during epochs proximate in time with the rare stimuli presentations are analyzed and therefrom an event-related potential (ERP) average magnitude is determined and is stored for analysis purposes.

A comparison 180 of the differences in magnitude of the brain signals obtained during the baseline period and those obtained during the task period is then done. According to the invention, the larger the difference in magnitude between the brain signals obtained during the baseline period and those obtained during the task period, the greater the interest of said subject has in said task stimuli. These brain signals will occur prior to those attributed to cognitive processing, and will fall approximately 0 to 200 milliseconds after the rare stimulus and at times during the period of 0 to 120 milliseconds after the rare stimulus.

In demonstrating the feasibility of the invention, electrophysiological data was confined to site FZ acquired ERP results that were obtained during a 30 second prevideo (pre-task) baseline and during the video (task) segments. Half of the 26 subjects tested were assigned to the HIGH interest group and half to the LOW interest group based on the questionnaire factor analysis previously described.

As described above, the video tape material presented included two 30-second video segments. After the video segments were shown to the subjects, the questionnaires were given as a cross-correlation of each subject's interest in the video material.

Figure 5:
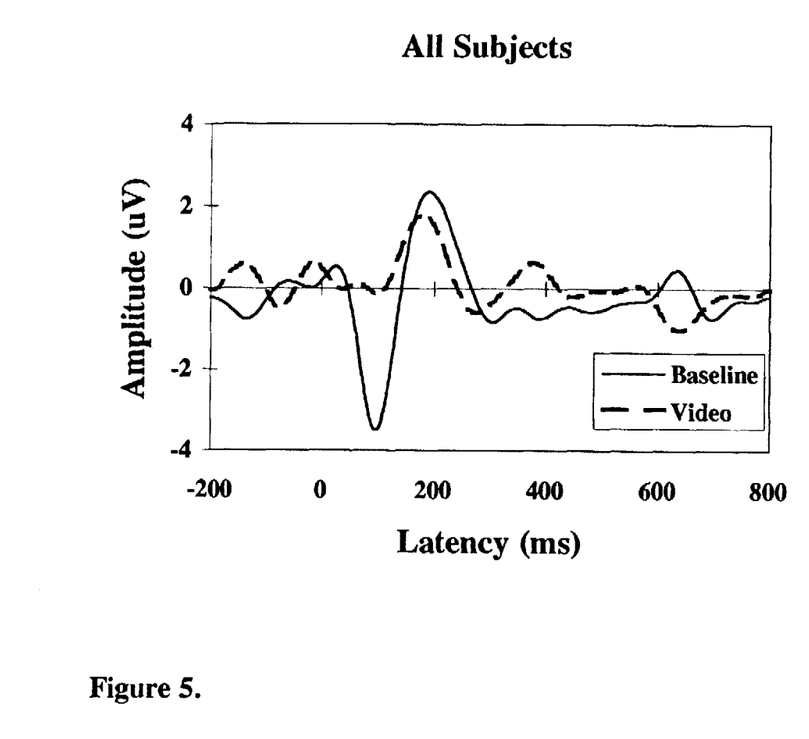
FIG. 5 depicts ERP data for all test subjects acquired from site FZ.

FIG. 5 shows an overlay of the grand average (all test subjects) waveforms for the 30 second pre-video baseline (solid line) with the 30 second video segment (broken line) as collected at the frontal site (FZ).

In FIG. 5, the component shown to be negative going at about 90 ms has been related to attentional factors in the literature. For the prevideo baseline and video task material comparisons, this component was statistically significant (t =−2.78, p<0.01, df=24 where t is the statistical test of difference in mean values, p is probability and df is degree of freedom). Data presented in FIG. 5 demonstrates that the irrelevant probe procedure used in the invention does in fact discriminate the prevideo recording condition from the video task material condition.

Figure 6:
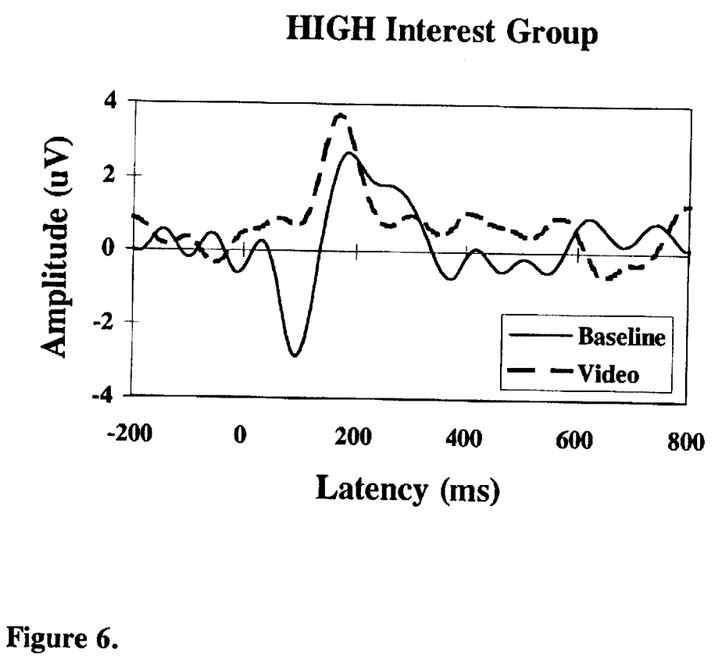
FIG. 6 is a comparison of prevideo and video material for the HIGH interest group.
Figure 7:
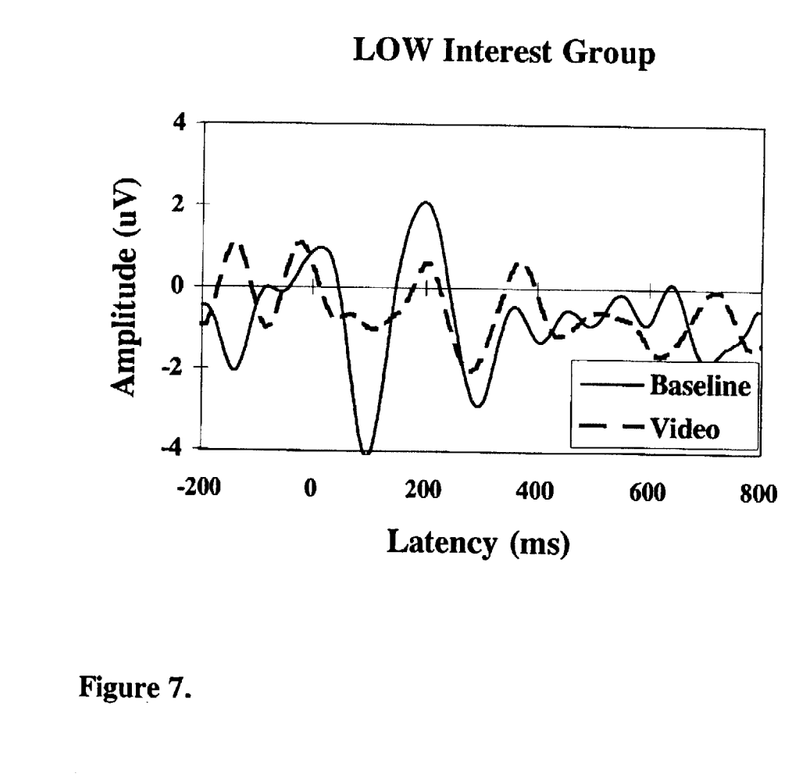
FIG. 7 is a comparison of prevideo and video material for the LOW interest group.

FIGS. 6 and 7 describe ERP waveforms for the HIGH interest and the LOW interest groups when prevideo baseline and video material ERPs are compared.

In a comparison of the HIGH group baseline ERPs and video task ERPs, FIG. 6 shows an overlay of the HIGH group grand average (all subjects) waveforms for the 30 second pre-video baseline ERP average (solid line) with the 30 second video task segment ERP average (broken line), both as collected at frontal site (FZ). Prevideo baseline versus video material comparisons were statistically reliable for the HIGH interest group (t=−2.23, p<0.025, df=24) for the component at about 90 ms.

The ERP component at about 90 ms was also statistically significant when the prevideo and video material comparisons were made for the LOW interest group, shown in FIG. 7, in which (t=−1.78, p<0.05, df=24).

A number of observations may be made for FIGS. 5, 6 and 7. The large negative component at about 90–100 ms may be seen in the baseline condition, but decreases significantly for the waveform obtained while the subjects watched the video segment. The decrease noted at FZ agrees with the literature in cortical topography of where this component is primarily located. All t-test values were negative, which implied that the video segment was more positive than the baseline recordings.

Figure 8:
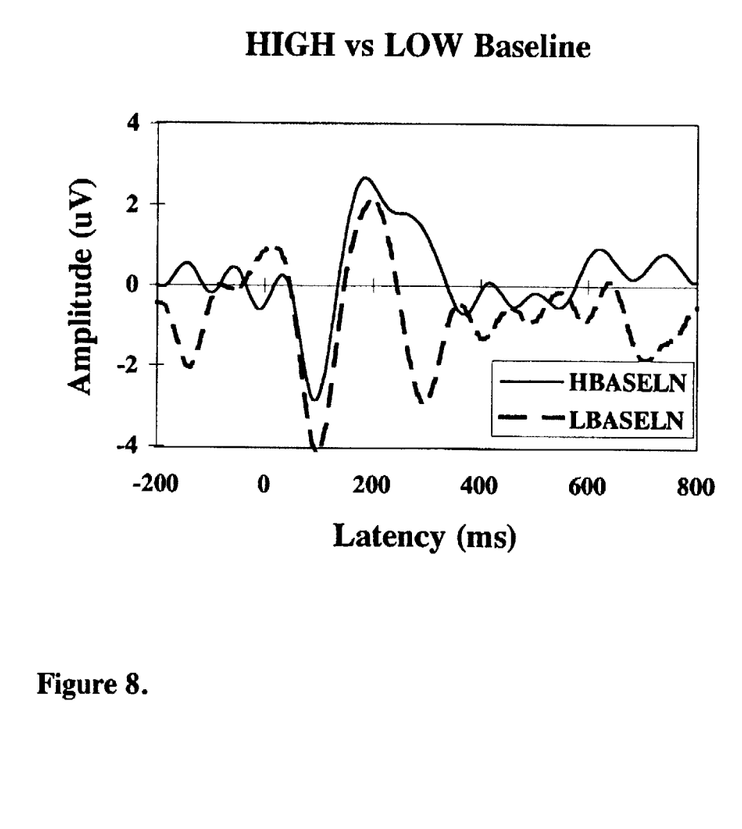
FIG. 8 is a comparison of HIGH versus LOW interest groups during prevideo baseline conditions.
Figure 9:
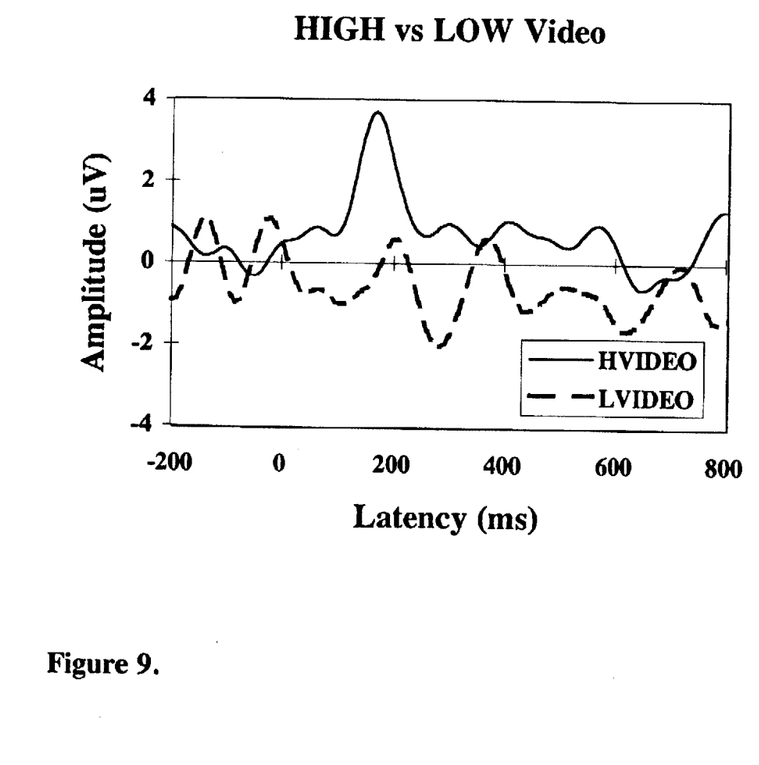
FIG. 9 is a comparison of HIGH and LOW interest groups ERPs acquired during the video presentations.

In order to differentiate ERP averages correlating to interest, FIGS. 8 and 9 overlay ERP averages for the HIGH interest group (solid line) with the LOW interest group (broken line). These data are the same data presented in earlier figures relating to baseline versus video comparisons for each of the two groups.

FIG. 8 illustrates a comparison of HIGH interest group baseline condition ERPs with that of the LOW interest group baseline condition ERPs. It may be seen that there are no significant differences between the HIGH and LOW interest groups for the components in the region of about 50 to 200 ms.

FIG. 9 illustrates a comparison of HIGH interest group video task ERPs with the LOW interest group video task ERPs and portrays a significant comparison for the present invention. The HIGH interst group versus LOW group interest group video task ERP comparison reflects the sensory and cognitive processing occurring during presentation of the drug abuse prevention training material.

Statistically significant differences were noted between the HIGH interest group and LOW interest group for the component at about 150 ms (t=2.59, p<0.01, df=24). In addition, the overall waveform for the HIGH interest group showed primarily to be positive voltage, while that for the LOW interest group was largely negative voltage.

The data suggests that the use of irrelevant probe stimuli, and resulting ERPs, can provide a mechanism for assessing attention, interest, and high level cognitive processing. Such stimuli provide an unobtrusive and objective measure of information.

This invention provides numerous advantages. The method is nonverbal. The subjects are not required to make any oral response about the materials they are asked to observe. Thus, the measure of personal interest is not dependent upon 22 interpretation of statements made by the subject.

Second, the method is unobtrusive. In the case in which an auditory probe is used, the probe is not loud, annoying, and does not interfere with the subject observing or using the materials reviewed, whether these be education, training or other materials. Thus, there is no apparent interaction between the task observed and the measurement of the subject's interest.

In addition, the method is surreptitious. There is no face validity to the method, and the subject does not know or is otherwise clued that interest is being measured in response to the probe. Thus, a subject cannot willingly manipulate the outcome of the measurement of interest.

The invention uses an irrelevant probe to generate a task-irrelevant neural response while a subject observes training, educational or other materials. The probe may be in a different modality than the task (e.g., auditory probe with visual or visual/auditory tasks).

The invention provides a new mechanism to estimate a subject's interest. There is currently no other known way to measure interest other than by asking the subject to indicate interest via verbal, questionnaire, or other test means.

Obviously, many modifications and variations of the invention are possible in light of the above teachings. It is therefore to be understood that within the scope of the appended claims the invention may be practiced otherwise than as has been specifically claimed.

what is claimed is:

1. A method comprising:
   presenting aperiodically during a baseline period first and second stimuli to a subject that was previously instructed to ignore said first and second stimuli, said second stimuli being presented less frequently than said first stimuli;
   obtaining from said subject during said baseline period first brain signals proximate in time with said second stimuli;
   determining the magnitude of said first brain signals;
   presenting to said subject task stimuli during a task period and aperiodically presenting to said subject first and second stimuli during said task period, wherein said subject was instructed prior to said task period to ignore said first and second stimuli and to pay attention to but not respond to said task stimuli;
   obtaining from said subject during said task period second brain signals proximate in time with said second stimuli;
   determining the magnitude of said second brain signals; and
   comparing the difference in magnitude of said first and second brain signals.

2. The method according to claim 1 in which the interest of said subject in said task stimuli is assessed in accordance with said difference.

3. The method according to claim 1 wherein the larger the difference in magnitude between said first and second brain signals, the greater the interest of said subject in said task stimuli.

4. A method according to claim 2 in which said difference is attributable to brain signals that occur within the range of 50 milliseconds to 200 milliseconds after said second stimuli begins.

5. A method according to claim 1 in which said first and second stimuli are auditory stimuli that are different in frequency.

6. A method according to claim 5 in which said first and second stimuli are auditory stimuli that are different by at least one octave in frequency.

7. A method according to claim 5 in which said task stimuli is video stimuli.

8. A method according to claim 6 in which said task stimuli is video stimuli.

9. A method according to claim 1 in which said brain signals are event-related potentials.

10. A method according to claim 1 in which said brain signals are event-related fields.

11. A method comprising:
    presenting aperiodically during a baseline period first and second audio stimuli to a subject that was previously instructed to ignore said first and second audio stimuli, said second audio stimuli being presented less frequently than said first audio stimuli;
    obtaining from said subject during said baseline period first brain signals proximate in time with said second audio stimuli;
    determining the magnitude of said first brain signals;
    presenting to said subject video stimuli during a task period and aperiodically presenting to said subject first and second audio stimuli during said task period, wherein said subject was instructed prior to said task period to ignore said first and second audio stimuli and pay attention to but not respond to said video stimuli;
    obtaining from said subject during said task period second brain signals proximate in time with said second audio stimuli;
    determining the magnitude of said second brain signals; and
    comparing the difference in magnitude of said first and second brain signals.

12. The method according to claim 11 in which said brain signals are event-related potentials.

13. The method according to claim 12 in which the interest of said subject in said video stimuli is assessed in accordance with said difference.

14. The method according to claim 12 wherein the larger the difference in magnitude between said first and second event-related potentials, the greater the interest of said subject in said task stimuli.

15. A method according to claim 13 in which said difference is attributable to brain signals that occur within the range of 50 milliseconds to 200 milliseconds after said second audio stimuli begins.

16. A method according to claim 12 in which said first and second audio stimuli are different in frequency.

17. A method according to claim 16 in which said first and second audio stimuli are different by at least one octave in frequency.

18. A method according to claim 11 in which said brain signals are event-related fields.

19. The method according to claim 18 in which said brain signals are event-related potentials.

20. The method according to claim 19 in which the interest of said subject in said video stimuli is assessed in accordance with said difference.

21. The method according to claim 19 wherein the larger the difference in magnitude between said first and second event-related potentials, the greater the interest of said subject in said task stimuli.

22. A method according to claim 21 in which said difference is attributable to brain signals that occur within the range of 50 milliseconds to 200 milliseconds after said second audio stimuli begins.

23. A method according to claim 19 in which said first and second audio stimuli are different in frequency.

24. A method according to claim 23 in which said first and second audio stimuli are different by at least one octave in frequency.

* * * * *